(12) United States Patent
Hsu et al.

(10) Patent No.: US 9,392,992 B2
(45) Date of Patent: Jul. 19, 2016

(54) HIGH INTENSITY FOCUSED ULTRASOUND REGISTRATION WITH IMAGING

(75) Inventors: Stephen J. Hsu, Issaquah, WA (US);
Liexiang Fan, Sammamish, WA (US);
Kevin Michael Sekins, Yarrow Point, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 60 days.

(21) Appl. No.: 13/407,638

(22) Filed: Feb. 28, 2012

(65) Prior Publication Data
US 2013/0225994 A1 Aug. 29, 2013

(51) Int. Cl.
*A61B 8/00* (2006.01)
*A61B 8/08* (2006.01)
*A61N 7/02* (2006.01)

(52) U.S. Cl.
CPC ... *A61B 8/08* (2013.01); *A61N 7/02* (2013.01); *A61B 2034/2063* (2016.02); *A61N 2007/027* (2013.01)

(58) Field of Classification Search
USPC .......... 600/407, 437, 411–413, 427–428, 439
See application file for complete search history.

(56) References Cited

U.S. PATENT DOCUMENTS

| 8,036,441 | B2 | 10/2011 | Frank et al. | |
|---|---|---|---|---|
| 2006/0004282 | A1* | 1/2006 | Oosawa | 600/416 |
| 2007/0106157 | A1* | 5/2007 | Kaczkowski et al. | 600/438 |
| 2007/0149880 | A1* | 6/2007 | Willis | 600/471 |
| 2008/0095421 | A1 | 4/2008 | Sun et al. | |
| 2008/0097207 | A1* | 4/2008 | Cai | 600/442 |
| 2008/0183077 | A1 | 7/2008 | Moreau-Gobard et al. | |
| 2008/0249419 | A1* | 10/2008 | Sekins et al. | 600/463 |
| 2009/0024034 | A1* | 1/2009 | Moreau-Gobard et al. | 600/443 |
| 2009/0287082 | A1 | 11/2009 | Lizzi et al. | |
| 2010/0317971 | A1 | 12/2010 | Fan et al. | |
| 2011/0060221 | A1 | 3/2011 | Fan et al. | |

FOREIGN PATENT DOCUMENTS

| CN | 101330874 | 11/2009 |
|---|---|---|
| EP | 2058028 | 5/2009 |
| WO | PCT/US2011/051485 | 9/2011 |

OTHER PUBLICATIONS

U.S. Appl. No. 13/024,574, filed Feb. 10, 2011.

* cited by examiner

*Primary Examiner* — Joel F Brutus

(57) ABSTRACT

High intensity focused ultrasound (HIFU) is registered with imaging. The effects of transmission from a HIFU transducer, such as a rise in temperature, are detected by a separate imaging system. By using multiple transmissions, a plurality of locations of the transmissions from the HIFU transducer are determined within the imaging system coordinates. A transform relating the imaging system coordinates to the HIFU transducer coordinates is determined from the detected effects. The transform may be used to relate locations indicated in images of the imaging system with coordinates of the HIFU transducer for application of HIFU. The imaging system may not have to scan the HIFU transducer or fiducials and a fixed relationship may not be needed.

16 Claims, 4 Drawing Sheets

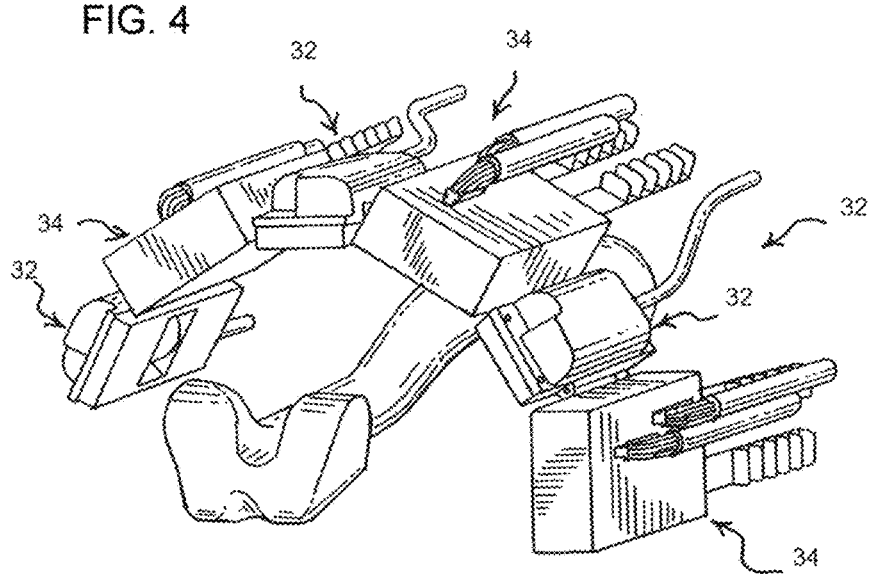

HIGH INTENSITY FOCUSED ULTRASOUND REGISTRATION WITH IMAGING

BACKGROUND

The present embodiments relate to high intensity focused ultrasound (HIFU). In particular, the treatment region from an image is determined for the HIFU system.

In HIFU therapy, a HIFU therapy device ablates by heat, and an imaging system monitors the progress of the ablation. The imaging system displays an image, allowing the user to indicate the desired target region for therapy. In order to dose the correct regions of interest, the imaging system's coordinates are registered with the HIFU therapy device's coordinates.

In an integrated system, the therapy transducer and imaging transducer have a set or fixed relative position. As a result, the transformation is static and therefore may be determined in advance. For systems where the imaging system may view the therapy device (e.g., the imaging scan includes scanning the HIFU transducer), the coordinate transformation may be determined from fiducial markers at known locations on the HIFU transducer. These fiducial markers are detected within images. A transform may be determined from the detected markers. However, in the circumstance where the relationship is not fixed, the fiducial markers are not available, and/or when the imaging device cannot see the HIFU transducer, an alternative method to determine the coordinate transformation is needed.

BRIEF SUMMARY

By way of introduction, the preferred embodiments described below include methods, computer readable media, instructions, and systems for registering high intensity focused ultrasound (HIFU) with imaging. The tissue effects of transmission from a HIFU transducer, such as a rise in temperature or displacement of tissue, are detected by a separate imaging system. By using multiple transmissions, a plurality of locations of the transmissions from the HIFU transducer are determined within the imaging system coordinates. A transform relating the imaging system coordinates to the HIFU transducer coordinates is determined from the detected effects. The transform may be used to relate locations indicated in images of the imaging system with coordinates of the HIFU transducer for application of HIFU. The imaging system may not have to scan the HIFU transducer or fiducials, and a fixed relationship may not be needed.

In a first aspect, a method is provided for registering high intensity focused ultrasound (HIFU) with imaging. A HIFU system transmits a sample of a high intensity focused ultrasound waveform to a first region of a patient. The sample has a different amplitude, duration, or both amplitude and duration from the waveform. An imaging system scans the first region of the patient. A response, such as temperature, due to the sample is detected from the scanning. A transform between coordinates of the HIFU system and coordinates of the imaging system is calculated. The transform is a function of a first location of the response caused by the transmitting to the first region as detected by the response. An image of the imaging system is displayed. User input of a treatment location relative to the image is received. The treatment location is transformed to the coordinates of the HIFU system with the transform. The waveform is focused as a function of the treatment location in the coordinates of the HIFU system and transmitted.

In a second aspect, a non-transitory computer readable storage medium has stored therein data representing instructions executable by a programmed processor for registering high intensity focused ultrasound (HIFU) with imaging. The storage medium includes instructions for transmitting, by a therapy device, a set of sonications to different therapy foci, detecting, by an imaging system, different detected foci of the sonications, and determining a coordinate transform between the therapy device and the imaging system as a function of the different therapy foci and detected foci.

In a third aspect, a system is provided for registering high intensity focused ultrasound (HIFU) with imaging. At least one therapy transducer is operable to transmit high intensity focused ultrasound. At least one imaging transducer is operable to transmit acoustic energy for imaging. A connector is between the at least one therapy transducer and the at least one imaging transducer. The connector is operable to conform to a patient. A processor is configured to determine a transformation between coordinates associated with the at least one therapy transducer and associated with the at least one imaging transducer. The transformation is a function of foci of the at least one therapy transducer detected with the at least one imaging transducer.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the Figures, like reference numerals designate corresponding parts throughout the different views.

FIG. 4 is a perspective view of a combination imaging and HIFU transducer system according to one embodiment.

DETAILED DESCRIPTION OF THE DRAWINGS AND PRESENTLY PREFERRED EMBODIMENTS

A set of sonications are transmitted by the therapy device into tissue. The tissue effects of the sonications are detected by the imaging system. Tissue effects include temperature and/or displacement. The detection provides a matched set of programmed foci of the therapy device and detected foci of the imaging system. The matched sets are used to determine a coordinate transformation (shift, scale, and/or rotate). Where the imaging system and therapy device are not rigidly positioned relative to each other and the imaging device may not adequately resolve the position of the therapy device, detecting effects of the therapy transmission by the imaging system may be used to spatially relate the corresponding coordinate systems.

Figure 1:
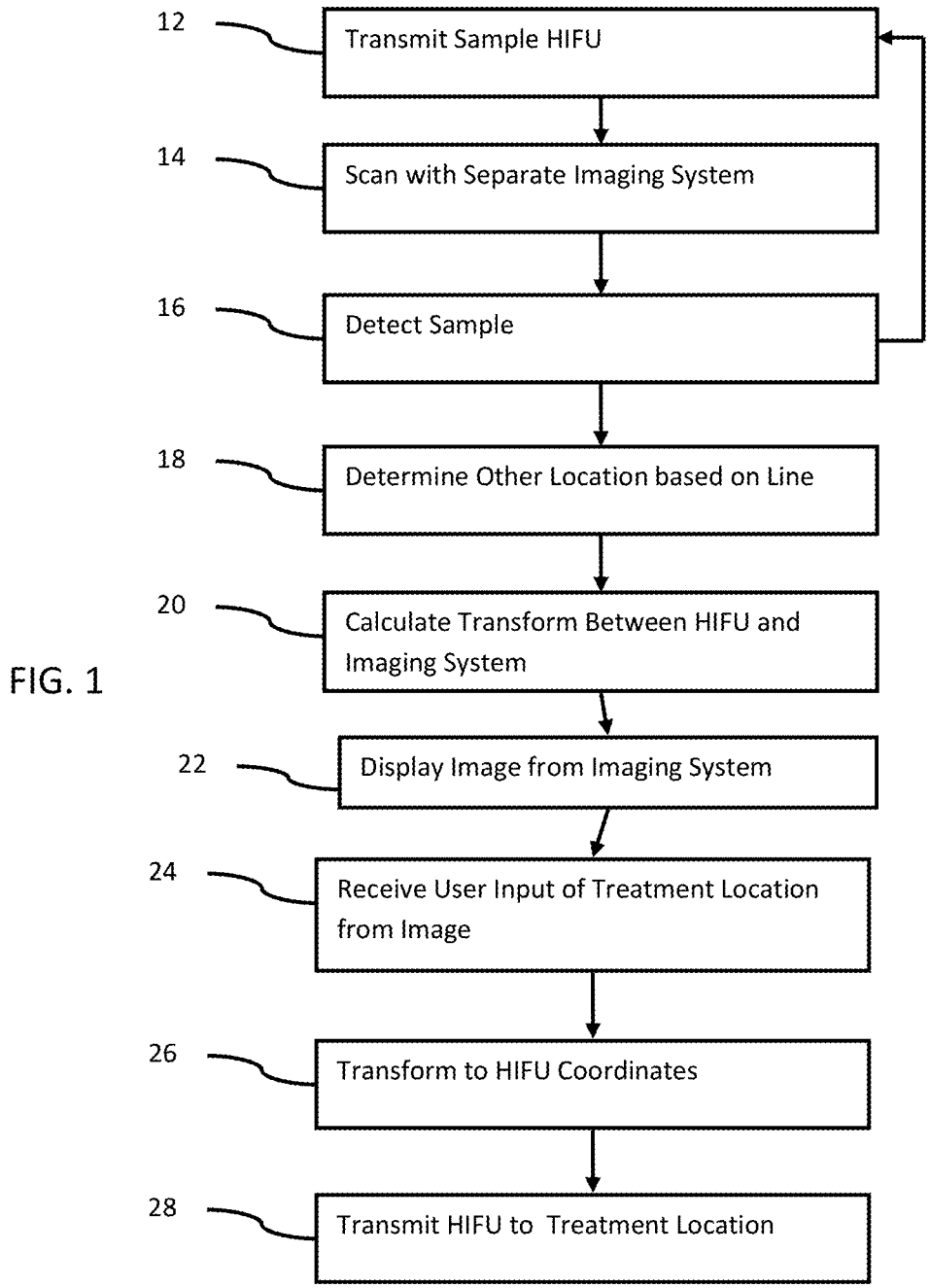
FIG. 1 is a flow chart diagram of one embodiment of a method of registering high intensity focused ultrasound (HIFU) with imaging.

FIG. 1 shows one embodiment of a method of registering high intensity focused ultrasound (HIFU) with imaging. The method provides for determining a transform between coordinate systems and use of the transform. In other embodiments, the transform is calculated without subsequent use. The method is implemented using the system of FIG. 3, 4, or 5, or a different system.

Additional, different, or fewer acts may be provided. For example, act 18 is optional. As another example, acts 12, 14, 16, and 20 are provided without at least acts 22, 24, 26, and 28. The acts are performed in the order shown or a different order.

The acts are performed for therapy. In a therapy session for a given patient, the patient is readied for the therapy. A sonographer or physician places one or more transducers on the patient. Before the high intensity focused ultrasound (HIFU) begins for ablation or other treatment, the transform to register the imaging system with the therapy device is determined. Since the relative positions of the imaging system and therapy device may be different for different patients or placements, the determination is performed to begin the therapy session. After the transformation is determined, the therapy may begin without repositioning of the therapy device and the imaging system. If the relative positions are changed, the transformation may be recalculated. The transformation may be recalculated in response to a trigger or periodically. Once thermal therapy begins, the transform calculation and/or use acts are repeated.

Using the transformation, locations for treatment identified from the images or data of the imaging system are transformed to coordinates of the therapy device. The therapy device is activated to treat the correct location based on the transform.

In act 12, a sample of a high intensity focused ultrasound therapy waveform is transmitted. The transmission is by the therapy device, such as a HIFU system. As a HIFU system, the therapy device includes a therapy transducer. In other embodiments, a different kind of transmission and device is provided for treating tissue of a patient.

For HIFU, the transmitted excitation is acoustic energy. The acoustic energy is focused, resulting in a three-dimensional beam profile with a focal location at a depth along the beam. The excitation is focused using a phased array and/or mechanical focus. The focus may be fixed or steerable. The excitation may be unfocused in one dimension, such as the elevation dimension. The excitation is transmitted into tissue of a patient. For a given transmission, a single beam is formed. Alternatively, multiple beams with respective foci are formed for a given transmission.

The excitation is generated as a therapy excitation. Alternatively, the excitation emulates the therapy excitation. A sample of the high intensity focused ultrasound therapy waveform is transmitted. A generally same focus, amplitude, frequency, and/or other characteristic as the therapy excitation are provided for the sample. The sample is used to substantially avoid therapeutic effect. For example, the amplitude, duration, or both are reduced as compared to a therapy waveform (e.g., $I_{sppa}$ on the order of about 200 W/cm$^2$ and duration on the order of about 600 micro seconds). "Substantially" avoiding therapeutic effect allows for generalization to a region, such as the region of treatment. A single point may be heated above a threshold level due to aberrations or focal distortion, but the treatment region overall avoids therapeutic effect from the emulation. Avoiding therapeutic effect may be avoiding heating to the point of altering the tissue or creating cavitations. For example, biological effects may include hyperthermia at tissue temperature of about 41-45° C., protein denaturation at temperatures above 45° C., and tissue necrosis at temperatures above 50° C. Tissue stiffness may be affected even at temperatures below 45° C. At temperatures above 45° C., increases in viscosity and/or stiffness may occur. At temperatures above 50° C., the tissue may have a high stiffness and/or high attenuation. Any limit on the emulation may be provided, such as attempting to prevent a temperature increase of five degrees or more Celsius.

The lower dose of the sample high intensity focused ultrasound therapy waveform causes a detectable response in the tissue. For example, the temperature at the focal region may increase in the range of 1-4 degrees, such as about 2-3 degrees. At locations other than the focal region, the temperature may increase less or not at all in response to the sample. As another example, the detectable response is tissue displacement. In alternative embodiments, the lower dose of the therapy waveform causes some therapeutic effect, such as increasing stiffness (e.g., raise the temperature to about 45° C.), but avoids other therapeutic effect (e.g., avoids raising the temperature to 50° C. or higher). The elasticity, strain, or stiffness of the tissue changes due to the sample.

In act 14, the imaging system scans the patient to detect the tissue response to the therapy sample. Any imaging system may be used. In one embodiment, the imaging system is a medical diagnostic ultrasound imaging system. The imaging system includes a transducer for scanning the patient. In another embodiment, the imaging system is a magnetic resonance system. Magnets and electrical pulses are used to detect the response of atoms or molecules. Other imaging modalities may be used, such as any modality capable of detecting the effect of the sample on the tissue. For example, both ultrasound and magnetic resonance systems may detect temperature or temperature changes in tissue. Displacement or other effects may also be detected.

The sensor of the imaging system, such as the transducer, is separate from the therapy device. Different housings are used for the transducers. In one embodiment, the therapy transducer and the imaging transducer are connected, but by a flexible or moveable structure. In another embodiment, no connection is provided. Handheld, robot held, fixed (e.g., positioned in a patient bed), or other separate fixtures may be provided for the sensors. Electronics or processors may or may not be shared, but the transducers defining the relative coordinate systems are not in fixed positions relative to each other.

In act 14, the imaging system scans the patient to detect, in act 16, the effect of the sample transmission of act 12. Any type of scan, scan format, or imaging mode may be used. For example, harmonic imaging is used with or without added contrast agents. As another example, B-mode, color flow mode, spectral Doppler mode, M-mode, or other imaging mode is used. Any mode of magnetic resonance may be used.

Data representing anatomical or other information is acquired from the patient. The data represents a point, a line, an area, or a volume of the patient. For ultrasound imaging, waveforms at ultrasound frequencies are transmitted, and echoes are received. The acoustic echoes are converted into electrical signals and beamformed to represent sampled locations within a region of the patient. The beamformed data may be filtered or otherwise processed. The beamformed data may be detected, such as determining intensity. A sequence of echo signals from a same location may be used to estimate velocity, variance, and/or energy. Echoes at one or more harmonics of the transmitted waveforms may be processed. The detected values may be filtered and/or scan converted to a display format. The ultrasound data representing the patient is from any point along the ultrasound processing path, such as channel data prior to beamformation, radio frequency or inphase and quadrature data prior to detection, detected data, or scan converted data.

The anatomical ultrasound information is the actual data. For example, B-mode data represents tissue structures. As another example, flow data indicates locations associated with a vessel. Alternatively or additionally, the anatomical ultrasound information is derived from the actual data. For example, the type of tissue at different locations is determined from a speckle characteristic, echo intensity, template matching with tissue structure, or other processing. As another example, region growing is used with B-mode data or color flow data to determine that the ultrasound data represents a vessel or other fluid region. A current distribution of anatomy, such as a list of represented organs, may be determined.

For magnetic resonance, the received data indicates projection intensities. Using tomography or other processing, the intensity of response from different locations is determined. Different pulse sequences may be used to detect different molecules and/or characteristics at the scan region.

The scan occurs during application of the sample or after application. For example, the scanning to detect temperature or temperature change may occur after transmission of the sample but before temperature equalization. As another example, the scanning occurs prior to and immediately after transmission of the sample to detect displacement of the tissue or change of temperature.

In act 16, the effect of the sample on the tissue is detected. For example, the temperature or temperature change due to the sample is detected. The imaging system detects the effect from the data obtained by scanning in act 14. The effect may be detected as a change in response or may be detected as an absolute (e.g., temperature).

In one embodiment, the detected effect is temperature. The sample causes a change in temperature greater at the focal region. The absolute temperature at the focal region may be greater than elsewhere in the region. The temperature or temperature change along the beam may be greater than outside the beam.

By performing thermometry by scanning and detecting, the temperature of various locations may be determined. Thermometry images or data is used to detect the temperature rise within the field of view associated with the sample.

Any temperature related measurement may be used. Ultrasound measurements may be provided for a plurality of different locations. Any now known or later developed temperature related measurement using ultrasound may be used. For example, tissue expands when heated. Measuring the expansion may indicate temperature. Temperature related measurements may directly or indirectly indicate a temperature. For example, a measure of a parameter related to conductivity or water content (e.g., a measurement of the type of tissue) may indirectly impact the temperature. The measurements may be for raw ultrasound data or may be derived from ultrasound data. In one embodiment, two or more, such as all four, of tissue displacement, speed of sound, backscatter intensity, and a normalized correlation coefficient of received signals are performed. Other measurements are possible, such as expansion of vessel walls.

Tissue displacement is measured by determining an offset in one, two, or three-dimensions. A displacement associated with a minimum sum of absolute differences or highest correlation is determined. The current scan data is translated, rotated, and/or scaled relative to a reference dataset, such as a previous or initial scan. The offset associated with a greatest or sufficient similarity is determined as the displacement. B-mode or harmonic mode data is used, but other data may be used. The displacement calculated for one location may be used to refine the search or search region in another location. Other measures of displacement may be used.

The speed of sound may be measured by comparison in receive time from prior to heating with receive time during heating. A pulse is transmitted. The time for the echo to return from a given location may be used to determine the speed of sound from the transducer to the location and back. Any aperture may be used, such as separately measuring for the same locations with different apertures and averaging. In another embodiment, signals are correlated. For example, in-phase and quadrature signals after beamformation are correlated with reference signals. A phase offset between the reference and current signals is determined. The frequency of the transmitted waveform (i.e., ultrasound frequency) is used to convert the phase difference to a time or speed of sound. Other measurements of the speed of sound may be used.

The backscatter intensity is B-mode or M-mode. The intensity or energy of the envelope of the echo signal is determined.

The normalized correlation coefficient of received signals may be measured. Beamformed data prior to detection, such as in-phase and quadrature data, is cross-correlated. In one embodiment, a reference sample or samples are acquired. During or after transmission of the sample, subsequent samples are acquired. For each location, a spatial window, such as three wavelengths in depth, defines the data for correlation. The window defines a length, area or volume. The current data is correlated with the reference data within the window space. The normalized cross-correlation is performed for the data in the window. As new data is acquired, further cross-correlation is performed.

Any temperature associated acoustic and physical parameters or changes in the parameters may be measured. Other measurements include tissue elasticity, strain, strain rate, motion (e.g., displacement or color flow measurement), or reflected power (e.g., backscatter cross-section).

In one embodiment, the temperature is estimated from a model rather than directly measured. One or more of the types of information discussed above may be used as inputs to the model. The actual data and/or derived information are anatomical parameters to be used in combination with the model. In addition to the ultrasound scanning, clinical or other information may be acquired for determining the temperature. For example, genetic information or other tissue related data may be mined from a patient record. Any feature contributing to determination of temperature related information may be used.

Expansion, shrinkage, water content, or other therapy parameters may indicate a current temperature. Regardless of the categorization of the measurement, the measurements are used as inputs to a model or to calculate values for input to the model. The data is provided for one or more locations, such as providing data for all locations in a two- or three-dimensional region. Alternatively, the data is generally associated with the entire region, such as one dose or energy level for the entire region.

The temperature related measurements are applied to a model. The measurements or data are input as raw data. Alternatively, the values (i.e., measurements and/or data) are processed and the processed values are input. For example, the values are filtered spatially and/or temporally. As another example, a different type of value may be calculated from the values, such as determining a variance, a derivative, normalized, or other function from the values. In another example, the change between the current values and reference or previous values is determined. A time-history of the values over a window of time may be used. The values are input as features of the model.

The output of the model may be used as an input. The values are applied during the application of the sample. For an initial application of the model, the feedback is replaced with a reference temperature, such as the temperature of the patient. For further application of the model, the previous output is fed back as an input, providing a time-dependent model. The temperature related information output by the model is fed back as a time history of the information, such as temperature at one or more other times. During transmission of the sample, the measured or received values are updated (i.e., current values are input for each application of the model), but previous values may also be used. The feedback provides an estimated spatial distribution of temperature or related information in the region at a previous time. The subsequent output of the model is a function of the ultrasound data or other values and a previous output of the modeling. The time-history of the values may be used as inputs, such that the time history and spatial distributions of the temperature-associated and therapeutic effect-related parameters are used as features of the model. In alternative embodiment, no feedback is used.

The model outputs a temperature or temperature distribution (i.e., temperature at different locations and/or times) from the input information. The derived temperature may be in any unit, such as degrees Fahrenheit or Celsius. The resolution of the temperature may be at any level, such as outputting temperature as in one of multiple two or other degree ranges. Alternatively, other temperature related information is output, such as a change in temperature, a dose, or an index value.

Any model may be used, such as a neural network or a piecewise linear model. The model is programmed or designed based on theory or experimentation. In one embodiment, the model is a machine-learned model. The model is trained from a set of training data labeled with a ground truth, such as training data associated with actual temperatures. For example, the various measures or receive data are acquired over time for each of multiple patients. During transmission of the sample therapy, the temperature is measured. The temperature is the ground truth. Through one or more various machine-learning processes, the model is trained to predict temperature given the values and/or any feedback.

Any machine-learning algorithm or approach to classification may be used. For example, a support vector machine (e.g., 2-norm SVM), linear regression, boosting network, probabilistic boosting tree, linear discriminant analysis, relevance vector machine, neural network, combinations thereof, or other now known or later developed machine learning is provided. The machine learning provides a matrix or other output. The matrix is derived from analysis of a database of training data with known results. The machine-learning algorithm determines the relationship of different inputs to the result. The learning may select only a subset of input features or may use all available input features. A programmer may influence or control which input features to use or other performance of the training. For example, the programmer may limit the available features to measurements available in real-time. The matrix associates input features with outcomes, providing a model for classifying. Machine training provides relationships using one or more input variables with outcome, allowing for verification or creation of interrelationships not easily performed manually.

The model represents a probability of temperature related information. This probability is a likelihood for the temperature related information. A range of probabilities associated with different temperatures is output. Alternatively, the temperature with the highest probability is output. In other embodiments, the temperature related information is output without probability information.

As an alternative to machine learning, manually programmed models may be used. The model may be validated using machine training. In one embodiment, a thermal distribution model is used. The thermal distribution model accounts for the thermal conductivity, density, or other behavior of different tissues, fluids, or structures. The thermal distribution model receives temperatures, temperature related information, measurements, or other data. The input information may be sparse, such as having temperature information for one or more, but fewer than all locations. The thermal distribution model determines the temperature at other locations. The thermal distribution model may determine the temperature at other times or both time and location.

In another embodiment, the thermal distribution model corrects temperatures based on anatomy. For example, a machine-learned model estimates temperature for uniform tissue. The temperature output is corrected to account for tissue differences in the region, such as reducing the temperature around thermally conductive vessels or fluid regions.

Figure 2:
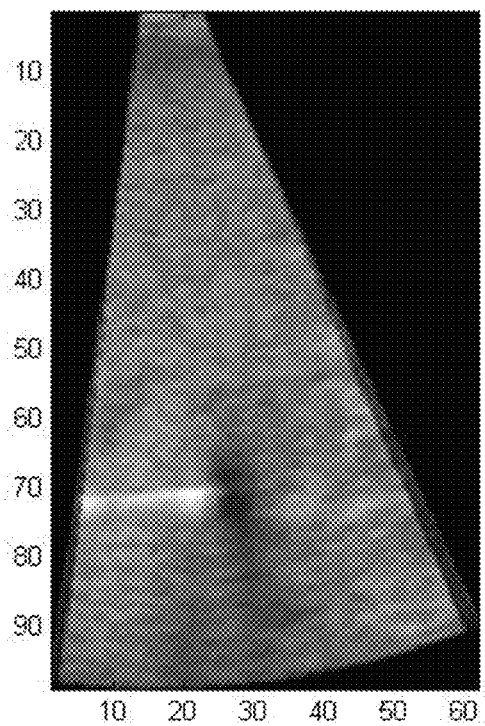
FIG. 2 is an example medical ultrasound image with a location of a temperature detected focus.

In response to input of the features, the model outputs the temperature related information, such as temperature. FIG. 2 shows a B-mode ultrasound image with a temperature overlay. The region in the lower center of the image is darker due to higher temperature. The darkest region corresponds to the highest temperature. Temporal persistence of the temperature may be used, such as maintaining a highest temperature where estimates are performed over time for each location.

The spatial distribution of temperature is used to identify a focal region within the imaging device's coordinates. Measurements are performed for multiple locations in a region. Full or sparse sampling may be used. The measurements are performed over time, but independent of previous measurements. Alternatively or additionally, a change in a measurement from a reference or any previous (e.g., most recent) measurement may be used.

Non-real time measurements may be used, such as a baseline temperature. MRI-based measurements for temperature distribution in a region may be used. Real-time measurements may be used, such as associated with ultrasound measurements performed during application of thermal therapy to a region of the patient.

A beam location or focal region for the HIFU is determined using the displacement of tissue information, temperature, or other characteristic. Locations associated with sufficient magnitude of displacement, temperature, strain, strain rate, shear, shear velocity, or shear modulus are identified. Where examples or embodiments use displacements, alternatively strain, strain rate, shear, shear velocity, or other derivatives of displacement may be used.

Locations where the displacement, temperature, or temperature change is relatively high are identified by applying a threshold. The threshold may be preprogrammed or adapted to a given data set. The threshold may be normalized, such as a threshold based on data at spatial locations spaced away from the likely location of the beam or focal region. As another example, an average or other percentage displacement or temperature across a region of interest is determined. Locations associated with a maximum displacement or temperature greater than the average or other percentage indicates beam or focal locations. The displacement or temperature data may or may not be spatially filtered prior to application of the threshold. The displacements or temperatures may be low pass filtered after application of the threshold. In other or additional embodiments, no threshold is applied, or a noise threshold is used.

The response of the tissue to the excitation is used to determine the scan line, focal point, or other sub-region of the displacements. The distribution indicates the center line, focal point, or any representative shape as affected by any aberrations, tissue differences, or other deviations from ideal. Multiple points or different lines may be calculated. In examples herein, point and line are used. Any manual, semi-automatic, or automatic approach to detecting the point, line or other region.

The line or point is determined within an area or a volume. For example, the location of the line or point is determined using temperatures representing a volume. The location of the point may be determined in a one dimensional region, such as the location being along a line. Temperature is measured for just the line or area, but may be measured for regions with additional dimensions even if not used to determine the location of the line or point.

The point may be calculated independently of the line. For example, a maximum temperature in a field of temperatures is determined. A center of a largest region of increased temperature, region growing, region shrinking, or other processes may be used to find the point. The point may be determined with or without segmentation. The point may be a center of gravity for a region, such as the largest segmented region of increased temperature. In one embodiment, the point is a maximum temperature value (e.g., highest echo strain value) along a line of higher temperature values. The temperatures along the line may be low pass filtered in addition to any other filtering before determining the location of the maximum or center.

The line of increased or higher temperatures represents the beam trajectory or scan line of the sample HIFU transmission. The beam trajectory line or curve is calculated rather than a simple center of focus. The line is calculated from the coordinates of the locations within the region. Region shrinking may be used, such as a skeleton operation on temperatures above a threshold. In one embodiment, a regression analysis is performed to fit a straight, curved or other line to the region. The line is through the center or other location of the region, indicating the location of the center of the sample HIFU beam.

FIG. 1 shows a feedback from act 16 to act 12. For transformation, multiple points and/or lines are identified. The transmission of the sample HIFU in act 12, scanning in act 14, and detection in act 16 are repeated for different locations. The sample HIFU is sequentially transmitted to different locations within an area or volume. A set of sonications is transmitted with different therapy foci. The focus for each transmission is changed to sample the area or volume. A low dose sonication pattern is transmitted into the region of interest.

The different foci of the sonications are detected. For example, the heating pattern associated with the sonication is detected by the imaging system for different foci. The repetition results in a matched set of therapy device foci and imaging system coordinates of detected foci.

Any number of repetitions may be used. For example, three foci are detected for a volume. More foci may be detected.

In act 18, other locations than the foci are identified in both coordinate systems. For further spatial diversity of the matched HIFU system foci to the detected foci by the imaging system, the line associated with the sample is used. Alternatively or additionally, an origin of the line is determined. The position where the beam trajectory emanates from the HIFU transducer is the origin. By using the line fitting and finding an end or intersection with an array, the origin is determined. The end may be found by a location where increased temperatures or displacement begins. The array may be detected with ultrasound return from the imaging system so that the intersection of the line with the array is found.

In another embodiment, the origin or another location is identified from a plurality of beam trajectories. The transmissions of sample HIFU to the different foci are controlled to emanate from a same location. The location is on the array, behind the array, or in front of the array. By line fitting to each beam trajectory, the point of intersection is found. The point of intersection is thus detected by data from the imaging system, such as derived from thermometry, and known based on the transmit parameters relative to the HIFU transducer.

Using one or more beam trajectories, one or more locations in addition to the foci known in both coordinate systems may be identified. For example, the intersection may indicate one location. One or more scan lines from that location may be used to find different origins on the HIFU transducer. A common origin or origin of a single line may be found without identification of the intersection. The beam trajectories may be used to extrapolate the center or position of the therapy device.

In act 20, a transform between coordinates of the HIFU system and coordinates of the imaging system is calculated. The transform registers the therapy transducer or device relative to the imaging system or transducer. A coordinate transform is determined, associating spatial locations relative to one system with spatial locations relative to another system. Given the registration, a location indicated in images or from data of the imaging system may be transformed to a location for the therapy system, allowing accurate identification of and application to a treatment region.

The transform is determined from the locations known to both systems. The foci of the sample transmissions detected by the imaging system provide matched locations in both systems. For example, the therapy system focuses the samples to locations defined in the coordinates of the therapy system. The temperature change, displacement, or other effect of the transmissions is detected from data in the imaging system, resulting in identification of the locations of the sample foci in the imaging system. The therapy system foci and the detected foci are at known locations in both systems. These matched locations are used to derive the transform relating the coordinate systems.

The transform may be calculated using other locations matched in both coordinate systems. For example, the beam trajectory (e.g., line or curve) is determined from the transmit parameters of the therapy system and detected by the imaging system. Origins, intersections or other matched locations may be used.

Any technique for registering coordinate systems may be used. In one embodiment, error minimization is performed. For example, a least squares analysis minimizes the error to align or spatially relate the same locations from the different coordinate systems. An error minimization algorithm may be used to determine a transformation between the programmed or set therapy device coordinates and detected imaging system coordinates. The error between matched locations, such as the foci used for the sample transmissions and detected by the imaging system, is minimized. As another example, a correlation, minimum sum of absolute differences, or other similarity measure is performed. The points and/or lines in both coordinate systems are translated, rotated, and/or scaled relative to each other. The translation, rotation, and/or scale resulting in the greatest correlation or minimum sum of differences is the transform.

The transformation provides for a translation, rotation, and/or scaling to associate coordinates or locations in one coordinate system with coordinates or locations in another coordinate system. The transformation may be an affine transformation. The transformation is a rigid shift of the entire coordinate systems. In another embodiment, the transform is calculated as a non-linear transform. For example, a 3-D spline interpolation is calculated between coordinates. The non-linear transform provides for warping, allowing different shifts for different locations. The calculated transform is a matrix, spline or other non-linear representation of the relationship between coordinate systems.

Acts 22-28 are for use of the transform. In act 22, an image is displayed. The image is acquired by the imaging system. The image is of a two-dimensional region of the patient. Alternatively, the image is a three-dimensional representation (i.e., two-dimensional image rendered from data representing a volume). In other embodiments, the image represents one spatial dimension (e.g., M-mode) or represents a sampling of individual range gates over time (e.g., spectral Doppler at one or more locations).

Any type of image may be used, such as a B-mode, color flow mode (e.g., Doppler velocity, energy, and/or variance), tissue Doppler, M-mode, spectral Doppler, harmonic mode, contrast agent, perfusion, elasticity, strain, strain rate, shear velocity, modulus, parametric, or other now known or later developed imaging. In one embodiment, anatomical information is displayed, such as a B-mode or harmonic B-mode image. Where the imaging system is a magnetic resonance system, other types of images may be provided.

The image may include the temperature related information. The temperature related information is displayed as a value, such as a temperature or dose. A graph of temperature as a function of time or along a line may be displayed. In one embodiment, the temperature is mapped to color and overlaid on a two-dimensional image or a three-dimensional representation. The mapping modulates the color as a function of the temperature related information, such as the shade of red or color between red and yellow being different for different temperatures. The change in temperature may alternatively be mapped to the output color or additionally mapped to brightness or other aspect of the color. The overlay is laid over an ultrasound image representing the anatomy, such as overlaid on a B-mode image. The overlay is registered to the anatomic information. The overlay indicates a current location of focus for the therapy system and the underlying anatomical image may show the anatomy to be treated.

The imaging system generates the image. The image is from data acquired as part of calculating the transform. Alternatively, the image is from data acquired after calculating the transform or interleaved during calculating of the transform.

In act 24, user input is received. Signals from a user interface, such as a touch screen, mouse or trackball and button, or arrow keys, are received.

The user indicates a treatment region relative the displayed image. For example, a single location (e.g., point) or multiple locations (e.g., line, area, or volume location) on the image is selected by the user. The location or locations are of anatomy that is to be treated. In alternative embodiments, a processor identifies the treatment region without user input. For example, the processor applies computer assisted diagnosis to find a lesion.

The user may input dose or other information as well. Various settings may be selected to provide a desired beam over the tissue to be treated while minimizing healthy tissue subjected to the HIFU.

In act 26, the selected treatment location is transformed from the imaging system coordinates to the therapy system coordinates. The treatment location is a one, two, or three-dimensional region of the patient. The locations for the selected region in the therapy system are determined by transforming the locations from the imaging system. Before subjecting the tissue to treatment, the position of the HIFU beam or therapy is determined. The focus for treatment is set to be at or relative to the locations identified from the imaging system.

The transformation is an interpolation or other mathematical calculation. Given a location in the imaging system, the translation, rotation, and/or scaling of the transform are applied to the location to determine the location in the therapy system. With the transformation, the therapy waveform is focused for the treatment location.

The transformation accounts for the independence of the therapy and imaging systems. For example, transducers for therapy and imaging are placed on the patient in a cuff or blanket. The transducers of the different systems are flexibly connected together, but the relative position is not known. Rather than or in addition to sensing fiducials or the arrays themselves, the temperature or effect measurement-based registration may be used. Rather than or in addition to using position sensors (e.g., angle measurement, optical measurement, magnetic position sensors or other devices), the effect measurement-based registration may be used.

In act 28, a therapy waveform is transmitted. The location of the focus, origin, scan line, or application of the therapy is based on the transformation. The coordinates in the therapy system for the treatment location of the patient are determined from the transformation. The dose, angle, focus, and/or other characteristics of the therapy are established for the treatment location.

In the HIFU embodiment, high intensity focused ultrasound therapy waveforms are transmitted. High voltage waveforms are applied to the high intensity focused ultrasound transducer, which generates the HIFU therapy waveforms in the acoustic domain. The HIFU pulse or pulses are focused using a phased array and/or mechanical focus and provide the high intensity acoustic energy to tissue at a focal or beam location.

The therapy provides a greater dose than the samples transmitted in act 12. The therapeutic ultrasound pulse has a plurality of cycles at any desired frequency and amplitude. In one embodiment, the therapeutic pulse lasts for a fraction of a second to seconds at an ultrasound frequency, such as 500 KHz-20 MHz. Any peak intensity may be provided, such as 100 or more watts per square centimeter, 500 or more watts per square centimeter, 1000-2000 watts per square centimeter, or about 1000 watts per square centimeter. Any now known or later developed therapeutic waveform with any intensity, frequency, and/or number of cycles may be used. The waveform is continuous or intermittent.

The therapeutic ultrasound pulse treats the tissue by generating heat at the desired tissue location. The intensity also generates stress on the tissue. The pulse pushes the tissue towards and away from the transducer with negative and positive acoustic pressures. For a sufficiently long therapeutic pulse, a substantially constant strain on the tissue is created. The strain, $\epsilon$, is a function of the tissue stiffness, $E$, the viscosity, $\eta$, and the stress from HIFU radiation force. The steady state stress during the therapeutic pulse is proportional to the ratio of average HIFU intensity, I, to the speed of sound in the tissue, c.

The HIFU waveforms may also generate biomechanical changes. The thermal effects of the therapy acoustic energy may cause changes in volume due to thermal expansion, in the speed of sound (c), in tissue stiffness (E), and/or in the viscosity (η) of fluids in the tissue. The therapy acoustic energy may also induce mechanical effects, such as radiation pressure, streaming, and/or cavitations. The biological effects may include hyperthermia at tissue temperature of about 41-45° C., protein denaturation at temperatures above 45° C., and tissue necrosis at temperatures above 50° C. Tissue stiffness may be affected even at temperatures below 45° C. At temperatures above 45° C., increases in viscosity and/or stiffness may occur. At temperatures above 50° C., the tissue may have a high stiffness and/or high attenuation.

The HIFU may be continuous or sporadic. Any treatment regimen may be used. During ongoing treatment or in between different fractions of the treatment, the imaging of act 22, input of act 24, and transformation of act 26 may be repeated. The therapy waveforms of act 28 are interleaved with the imaging of act 22. The HIFU treatment ceases while the beam location is determined. In another alternative, the HIFU is performed at one frequency or coding, and the transmission of the excitations and corresponding reception for imaging are performed at a different frequency or coding, allowing operation at the same time. The interleaving allows user or system positioning of the HIFU beam on an on-going basis. If the patient or transducer shifts position, the beam may be altered to treat the appropriate tissue. If the speed of sound in the tissue changes due to the treatment, the beam may be altered to treat the appropriate tissue.

The transformation is calculated once or is also updated. For example, the patient or transducer positions may shift. The transformation may be updated to account for such changes of alignment between the coordinate systems.

Figure 3:
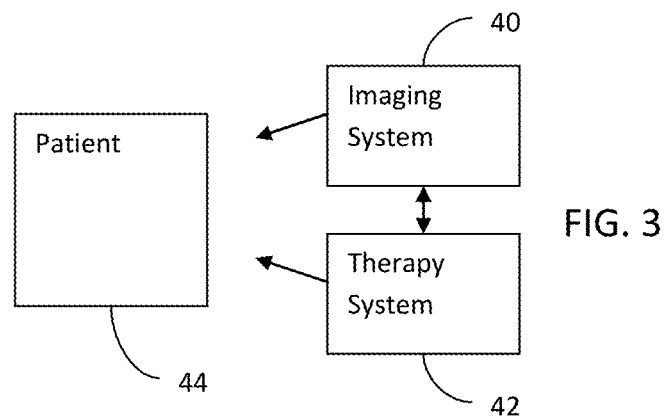
FIG. 3 is a block diagram of one embodiment of a system for registering high intensity focused ultrasound (HIFU) with imaging.

FIG. 3 shows one embodiment of a system for registering high intensity focused ultrasound (HIFU) with imaging. The system performs the method described above or a different method. Other systems may be used.

The system includes an imaging system 40 and a therapy system 42 for use with the patient 44. The imaging system 40 is a magnetic resonance, diagnostic ultrasound, x-ray, computed tomography or other imaging system. The therapy system 42 is a HIFU system, microwave system, radiation system, or other source of transmitted therapeutic energy.

The imaging system 40 and therapy system 42 are separate systems. The coordinates of the systems 40, 42 are different. For example, separate transducers are used for therapy and imaging.

The systems 40, 42 communicate to allow calculation of a transform. The location or coordinate information of one system is communicated to the other system. Alternatively, predetermined foci and corresponding coordinate information of the therapy system 42 are known or stored in the imaging system 40.

A processor in one of the systems calculates the transform. Alternatively, a separate computer is provided for calculating the transform. For example, a personal computer, workstation, or server calculates the transform from data received from one or both of the systems 40, 42.

Figure 5:
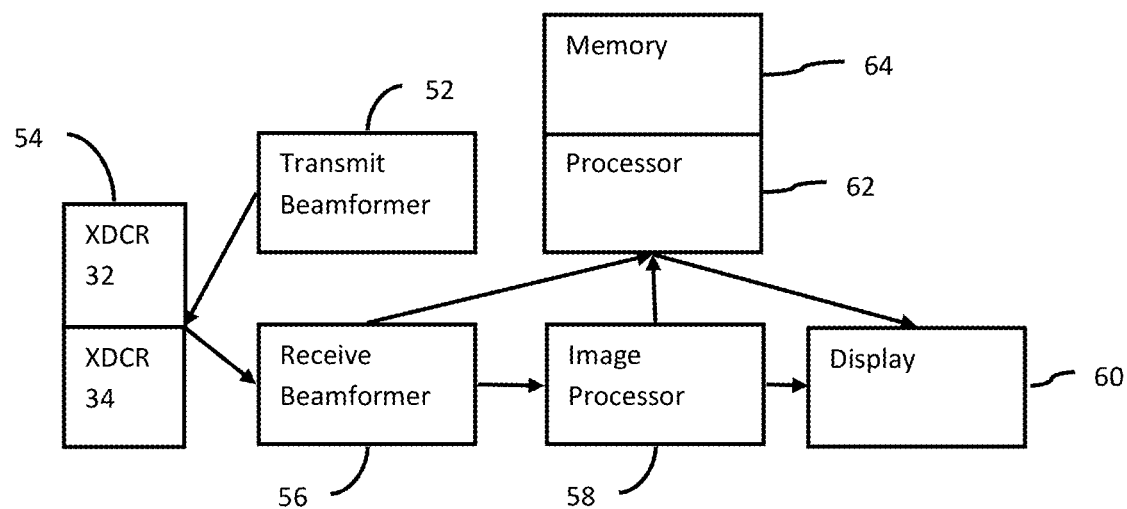
FIG. 5 is a block diagram of one embodiment of a medical diagnostic ultrasound imaging system.

Some components may be shared, such as processing electronics. In one embodiment, separate transducers are used, but otherwise the processing is performed by a common system. FIG. 4 shows one example arrangement of separate transducers 32, 34. FIG. 5 shows one example ultrasound system for operating the transducers 32, 34 of FIG. 4 or other therapy and imaging transducer arrangement.

The ultrasound system of FIG. 5 includes a transmit beamformer 52, a transducer 54, a receive beamformer 56, an image processor 58, a display 60, a processor 62 and a memory 64. Additional, different or fewer components may be provided. For example, separate detectors and a scan converter are also provided. As another example, a separate transmit beamformer is provided for therapy.

The ultrasound system is a medical diagnostic ultrasound imaging system. Imaging includes two-dimensional, three-dimensional, B-mode, Doppler, color flow, spectral Doppler, M-mode or other imaging modalities now known or later developed. The ultrasound system is a full size cart mounted system, a smaller portable system, a hand-held system or other now known or later developed ultrasound imaging system. In another embodiment, the processor 62 and memory 64 are part of a separate system. For example, the processor 62 and the memory 64 are a workstation or personal computer operating independently of the ultrasound system. As another example, the processor 62 and the memory 64 are part of the therapy system 42.

The transducer 54 includes one or more therapy transducers 32 (see FIG. 4). The therapy transducer 32 is any now known or later developed transducer for generating high intensity focused ultrasound from electrical energy. A single element may be provided, such as where focus is provided mechanically by movement or a lens. A plurality of elements in a one or multi-dimensional array may be used, such as an array of N×M elements where both N and M are greater than 1 for electric based focusing or steering.

The element or elements are piezoelectric, microelectro-mechanical, or other transducer for converting electrical energy to acoustic energy. For example, the therapy transducer 32 is a capacitive membrane ultrasound transducer.

The therapy transducer 32 is operable from outside a patient. For example, the therapy transducer 32 is a probe or other device held against the patient's skin. The therapy transducer 32 is handheld, positioned by a device, or strapped to the patient. In other embodiments, the therapy transducer 32 is in a probe, catheter or other device for operation from within a patient.

In one embodiment, only one therapy transducer 32 is provided. In other embodiments, a plurality of therapy transducers 32 is provided. For example, a plurality of two-dimensional arrays of elements is used for transmitting from different locations to a treatment region. FIG. 4 shows a cuff structure with at least three therapy transducers 32.

Each of the transducer elements connect to the transmit beamformer 52 for receiving electrical energy from the transmit beamformer 52. The therapy transducer 32 converts the electrical energy into an acoustic beam for therapy or for sampling.

The transducer 54 (see FIG. 5) includes one or more imaging transducers 34 (see FIG. 4). The imaging transducer 34 is the same or different type, material, size, shape, and structure than the therapy transducer 32. For example, one or more imaging transducers 14 each include a multi-dimensional array of ultrasound transducer elements. The imaging transducer 34 is any now known or later developed transducer for diagnostic ultrasound imaging. The imaging transducer 34 is operable to transmit and receive acoustic energy.

In one embodiment, only one imaging transducer 34 is provided. In other embodiments, a plurality of imaging transducers 34 is provided. For example, a plurality of two-dimensional arrays of elements is used for transmitting from different locations to a patient region including a treatment region. FIG. 4 shows a cuff structure with at least three imaging transducers 34.

The therapy and imaging transducers 32, 34 are separate from each other. A fixed or known relative position is not provided. Different flexible cables may connect the transducers 32, 34 with the same electronics, but the cables to not dictate relative position other than limiting a distance apart that may occur.

In another embodiment, the therapy transducer 32 connects with the imaging transducer 34, but not fixedly. A connector is flexible or moveable. For example, the therapy and imaging transducers 32, 34 are in a cuff or blanket (see FIG. 4). The blanket is plastic, metal, fabric, or other material for rigidly, semi-rigidly or flexibly holding the plurality of transducers 32, 34 with or without the beamformers 52, 56, and/or processor 62. For example, FIG. 4 shows a blanket with a plurality of transducers 32, 34. Hinges, other structure, or an outer casing interconnect the transducers 32, 34. For example, hinges connect the transducers 32, 34. One or more sets of transducers 32, 34 may be more rigidly connected.

The blanket includes every other transducer as an imaging transducer 34 and a therapy transducer 32. Other ratios and/or arrangements may be provided. One, more, or all of the transducers may be dual use devices, such as each transducer 32, 34 being for imaging and therapy. In one embodiment, each of the imaging transducers 34 is operable to electronically or electronically and mechanically scan in three dimensions for acquiring data representing a volume. The transducers 34 may be arranged such that, at least for deeper depths, the scan volumes of adjacent imaging transducers 34 overlap.

A covering, such as a fabric, plastic or other material, may relatively connect the transducers 32, 34. The blanket is a cuff or other structure for wrapping around or resting on a patient. FIG. 4 shows the blanket of transducers 32, 34 wrapped at least partially around a leg or arm, represented by a bone. The ultrasound devices are embedded in a flexible surface, wrapped around the region of the body needing medical attention. This geometry may allow acquiring 360-degree images around a limb or larger volumes than with a single array of transducer arrays.

Depending on placement, the relative position of the therapy transducers 32 and the imaging transducers 34 may be different. The spatial relationship between the transducers 32, 34 is measurable. The registration and corresponding transformation calculation may be performed after placement on the patient. Sample treatment is performed and the resulting effect (e.g., temperature or change) is detected. The matched locations from the transmission and detection are used to calculate the transformation.

Additional indications of the relative positions may be measured. For example, a sensor measures the relative motion between the two. Any sensor may be used, such as magnetic position sensors, strain gauges, fiber optics, or other sensor. Alternatively or additionally, acoustic response from the arrays indicates the relative positions. Fiducials may be used. Correlation of imaging data may indicate a spatial relationship between imaging transducers 34. In other embodiments, the same array is used for both therapy and imaging, so data correlation indicates the spatial relationship for imaging and therapy transducers 32, 34. The additional position indications are used as yet further information for determining the transform. Alternatively, separate transforms are provided and the results averaged.

The transmit beamformer 52 is one or more ultrasound transmitter, memory, pulser, waveform generators, amplifiers, delays, phase rotators, multipliers, summers, digital-to-analog converters, filters, combinations thereof and other now known or later developed transmit beamformer components. The transmit beamformer 52 is configured into a plurality of channels for generating transmit signals for each element of a transmit aperture. The transmit signals for each element are delayed and apodized relative to each other for focusing acoustic energy along one or more scan lines. Signals of different amplitudes, frequencies, bandwidths, delays, spectral energy distributions or other characteristics are generated for one or more elements during a transmit event.

The transmit beamformer 52 connects with the therapy transducer 32 and/or the imaging transducer 34. In one embodiment, the same transmit beamformer 52 is used for both. In other embodiments, different or separate transmit beamformers 52 are used.

For imaging, the transmit beamformer 52 transmits a plurality of beams in a scan pattern. Upon transmission of acoustic waves from the transducer 34 in response to the generated waves, one or more beams are formed. A sequence of transmit beams are generated to scan a two or three-dimensional region. Sector, Vector®, linear, or other scan formats may be used. The same region is scanned multiple times. For flow or Doppler imaging and for strain imaging, a sequence of scans is used. In Doppler imaging, the sequence may include multiple beams along a same scan line before scanning an adjacent scan line. For strain imaging, scan or frame interleaving may be used (i.e., scan the entire region before scanning again). In alternative embodiments, the transmit beamformer 52 generates a plane wave or diverging wave for more rapid scanning.

For therapy, the transmit beamformer 52 transmits one or more beams. To calculate the transform, the acoustic beams are samples of high intensity focused ultrasound waveforms. The samples have lesser aperture, amplitude, frequency or combinations thereof than used for therapy. The samples emulate the HIFU waveforms and are sufficient to increase temperature or cause other detectable effect to the tissue (e.g., displacement).

The samples are transmitted to different foci regardless of treatment region. The foci are distributed randomly or regularly throughout a volume or area of interest. A set of samples are transmitted.

For actual therapy, the transmit beamformer 52 causes generation of acoustic energy for HIFU. The high intensity focused ultrasound transducer 34 generates high intensity focused ultrasound therapy waveforms. Relative delays focus the acoustic energy. A given transmit event corresponds to transmission of acoustic energy by different elements at a substantially same time given the delays. The transmit event provides a pulse of ultrasound energy for treating the tissue. The transmit event may be repeated or may include on-going (multiple cycle) waveforms.

The receive beamformer 56 is configured to acquire ultrasound data representing a region of a patient. The ultrasound data is for measuring temperature related information, acquiring anatomical information, detecting displacement, and/or receiving other data. The anatomical information is, at least in part, from ultrasound data.

The receive beamformer 56 includes a plurality of channels for separately processing signals received from different elements of the transducer 54. Each channel may include delays, phase rotators, amplifiers, filters, multipliers, summers, analog-to-digital converters, control processors, combinations thereof and other now known or later developed receive beamformer components. The receive beamformer 56 also includes one or more summers for combining signals from different channels into a beamformed signal. A subsequent filter may also be provided. Other now known or later developed receive beamformers may be used. Electrical signals representing the acoustic echoes from a transmit event are passed to the channels of the receive beamformer 56. The receiver beamformer 56 outputs in-phase and quadrature, radio frequency or other data representing one or more locations in a scanned region. The channel data or receive beamformed data prior to detection may be used by the processor 62.

The receive beamformed signals are subsequently detected and used to generate an ultrasound image by the image processor 58. The image processor 58 is a B-mode/M-mode detector, Doppler/flow/tissue motion estimator, harmonic detector, contrast agent detector, spectral Doppler estimator, combinations thereof, or other now known or later developed device for generating an image from received signals. The image processor 58 may include a scan converter. The detected or estimated signals, prior to or after scan conversion, may be used by the processor 62.

The display 60 is a monitor, LCD, plasma, projector, printer, or other now known or later developed display device. The display 60 is configured to display an image representing the region of the patient and/or the effect of thermal therapy. For example, an anatomy image is displayed. As another example, temperature or related information is output as a value, graph, or two-dimensional representation. The processor 62 and/or the image processor 58 generate display signals for the display 60. The display signals, such as RGB values, may be used by the processor 62.

The processor 62 is a control processor, beamformer processor, general processor, application specific integrated circuit, field programmable gate array, digital components, analog components, hardware circuit, combinations thereof and other now known or later developed devices for processing information. The processor 62 is configured, with computer code, to identify locations of effect from a sample therapy transmission. For example, the processor 62 models an effect of thermal therapy on a treatment region. The temperature for one or more locations in the treatment region is estimated based on inputs to the model. The computer code implements a machine-learned model and/or a thermal model to estimate the temperature or temperature related information. The model is a matrix, algorithm, or combinations thereof to estimate based on one or more input features. In one embodiment, the processor 62 estimates temperature information as disclosed in U.S. Patent Application No. 2011/0060221, the disclosure of which is incorporated herein by reference. In other embodiments, the processor 62 uses measurements of one or more parameters to estimate temperature without a model.

The processor 62 detects various foci of sample HIFU transmissions from the temperature or other imaging-based information. For example, data received from the receive beamformer 56 is used to detect locations associated with peak heating caused by the low dose of high intensity focused ultrasound or other therapy. The beam trajectory or scan line for one or more samples may be detected. The origin and/or intersection of trajectories may be detected.

The processor 62 determines a transformation between coordinates associated with the therapy transducers 32 and associated with the imaging transducer 34. The transform may be for a given therapy transducer 32 to another imaging transducer 34 or for groups thereof. In one embodiment, transforms for all of the transducers 32, 34 to a common grid or coordinate system may be calculated. The imaging transducers 34 may be on a common coordinate system, such as by using data correlation from the different transducers 34 to detect relative positions. One or more of the therapy transducers 32 are registered with the imaging coordinate system.

The transformation is a function of the foci of the samples transmitted from the therapy transducers 32 and detected with the imaging transducers 34. Using the foci from both systems, the error between coordinate spaces is minimized. Any type of transform may be calculated.

The processor 62 uses the transform to direct therapy to a treatment region identified from images of the imaging system 40. A treatment location on an image acquired with the imaging transducer or transducers 34 is received. A therapy location for transmission of the high intensity focused ultrasound from one or more of the therapy transducers 32 is determined with the transform. The locations in the imaging system 40 are transformed to locations in the therapy system 42. The processor 62 then causes the transmission of the high intensity focused ultrasound to the therapy location. The locations are transmitted to the therapy system 42 or used to control for focus of the therapy system 42.

The memory 64 is a non-transitory computer readable storage medium having stored therein data representing instructions executable by the programmed processor for registering high intensity focused ultrasound (HIFU) with imaging. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method of registering high intensity focused ultrasound with imaging, the method comprising:
    transmitting, from a high intensity focused ultrasound system, a sample of a high intensity focused ultrasound waveform to a first region of a patient, the sample having a different amplitude, duration, or both amplitude and duration from but same focus as the high intensity focused ultrasound waveform;
    scanning, with an imaging system, the first region of the patient;
    detecting a response due to the sample, the detecting being from the scanning;

calculating a transform between a coordinate system of the high intensity focused ultrasound system and a coordinate system of the imaging system, the transform mathematically relating locations of the coordinate system of the imaging system with locations of the coordinate system of the high intensity focused ultrasound system, and the transform being a function of a first location of the response in the first region of the patient caused by the transmitting to the first region of the sample by the high intensity focused ultrasound system as detected from the scanning by the imaging system;

displaying an image of the imaging system;

receiving user input of a treatment location relative to the image;

transforming the treatment location to coordinates of the high intensity focused ultrasound system with the transform; and transmitting the waveform focused as a function of the treatment location in coordinates of the high intensity focused ultrasound system.

2. The method of claim 1 further comprising repeating the transmitting, scanning and detecting for at least second and third locations, wherein calculating the transform comprises calculating as a function of the first, second and third locations.

3. The method of claim 1 wherein the first location is part of a beam trajectory, the transform calculated as a function of the beam trajectory including the first location.

4. The method of claim 3 further comprising determining an origin of the beam trajectory, wherein calculating comprises calculating the transform as a function of the origin.

5. The method of claim 1 wherein calculating comprises performing an error minimization.

6. The method of claim 1 wherein calculating comprises determining a translation, rotation, and scaling for affine transformation.

7. The method of claim 1 wherein calculating comprises calculating the transform as a non-linear transform.

8. The method of claim 1 wherein transmitting the sample comprises transmitting a lower dose of the high intensity focused ultrasound waveform, and wherein transmitting the waveform comprises transmitting a higher dose of the high intensity focused ultrasound waveform.

9. The method of claim 1 wherein scanning and detecting comprise performing thermometry, the response comprising temperature.

10. The method of claim 9 wherein performing the thermometry comprises performing ultrasound thermometry.

11. The method of claim 1 wherein the high intensity focused ultrasound system comprises a therapy transducer, wherein the imaging system comprises an imaging transducer separate from but flexibly connected with the therapy transducer, wherein calculating the transform comprises registering the therapy transducer relative to the imaging transducer, and wherein the transforming accounts for the flexibly connection such that the waveform is focused at the treatment location.

12. A system for registering high intensity focused ultrasound with imaging, the system comprising:

at least one therapy transducer operable to transmit high intensity focused ultrasound;

at least one imaging transducer operable to transmit acoustic energy for imaging;

a connector between the at least one therapy transducer and the at least one imaging transducer, the connector operable to conform to a patient; and a processor configured to determine a transformation between a coordinate system associated with the at least one therapy transducer and a coordinate system associated with the at least one imaging transducer, the transformation mathematically relating locations of the coordinate system of the imaging system with locations of the coordinate system of the high intensity focused ultrasound system, and the transform being a function of foci of the at least one therapy transducer detected with the at least one imaging transducer.

13. The system of claim 12 wherein the at least one therapy transducer comprises a first multidimensional array of elements and wherein the at least one imaging transducer comprises a second multidimensional array of elements;

further comprising:

a transmit beamformer configured to generate a set of low dose sonications focused at the foci of the at least one therapy transducer;

a receive beamformer configured to scan a region of the patient;

wherein the processor is configured to detect the foci from data received from the receive beamformer.

14. The system of claim 12 wherein the processor is configured to detect locations associated with heating caused by a low dose of the high intensity focused ultrasound, the locations comprising the foci.

15. The system of claim 12 wherein the at least one therapy transducer comprises a plurality of therapy transducers, wherein the at least one imaging transducer comprises a plurality of imaging transducers interleaved with the therapy transducers, and wherein the connector comprises a flexible cuff.

16. The system of claim 12 wherein the processor is configured to receive a treatment location on an image acquired with the at least one imaging transducer, determine a therapy location for transmission of the high intensity focused ultrasound from the at least one therapy transducer with the transform, and cause transmission of the high intensity focused ultrasound to the therapy location.

* * * * *